United States Patent [19]

Ramachandran

[11] Patent Number: 5,061,810
[45] Date of Patent: Oct. 29, 1991

[54] SUBSTITUTED BENZOPHENONE DICARBOXYLIC ACIDS

[75] Inventor: Venkataraman Ramachandran, Baton Rouge, La.

[73] Assignee: Ethyl Corporation, Richmond, Va.

[21] Appl. No.: 443,129

[22] Filed: Nov. 28, 1989

[51] Int. Cl.$^5$ .................. C07D 493/00; C07C 49/76
[52] U.S. Cl. ........................ 549/244; 560/52; 562/460; 568/332
[58] Field of Search ............ 549/244; 568/332; 562/460; 560/52

[56] References Cited

U.S. PATENT DOCUMENTS 3,287,373  11/1966  McCracken .................. 549/242

FOREIGN PATENT DOCUMENTS 1565700  5/1969  France .................. 549/242
1601094  9/1970  France .................. 549/242

OTHER PUBLICATIONS

Mirono et al., "4-(3,4-Diamino-benzoyl)phthalic anhydride" J. Org. Chem. USSR 9 (1973) 121-125.
Mirono et al., "Synthesis of benzophenone..." CA 78 (17) 110140p (1973).
Drechsler, "Polybenzyl benzenes .." CA 62:10360d (1965).
Krasovitskii, "Dyes for dyeing ..." CA 57:12673a (1960).

Primary Examiner—C. Warren Ivy
Assistant Examiner—Celia Chang
Attorney, Agent, or Firm—Richard J. Hammond

[57] ABSTRACT

Substituted benzophenones are disclosed having the following formula

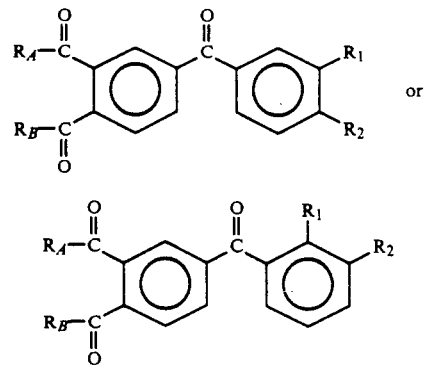

where $R_A$ and $R_B$ are —OH, $C_1$ to $C_{12}$ linear or branched alkoxy or taken together with the adjacent carbonyl carbons form an anhydride ring, $R_1$ and $R_2$ are the same or different and are hydrogen, $C_1$ to $C_6$ linear or branched alkyl, halo, aryl unsubstituted or substituted with one or more aryloxy groups or $R_1$ and $R_2$ taken together are $(CH_2)_x$ where x is an integer from 3 to 6 with the proviso that $R_1$ and $R_2$ cannot both be hydrogen.

Processes to produce these benzophenones are also disclosed.

7 Claims, No Drawings

SUBSTITUTED BENZOPHENONE DICARBOXYLIC ACIDS

The present invention relates to aromatic ketones and methods for preparing such ketones. More particularly, this invention relates to substituted benzophenone dicarboxylic acid, acid esters and acid anhydrides and methods of their preparation.

Linear aromatic or heterocyclic condensation-type polyimides have been an item of commerce for over two decades. The polymer systems that have shown the most success are those that utilize the reaction product of an aromatic dianhydride and aromatic diamine. Because of the difficulty in shaping, coating or other processing of the polyimides produced from the above starting materials, it has been found more convenient to first form a solution of polyamic acid intermediate, and then to thermally or chemically imidize this intermediate. It has further been found that the control of the physical properties e.g. viscosity of the intermediate can be more easily effected if an end-capping agent is added to the reaction system. These end-capping agents are typically used to carboxylate the terminal amino groups of the developing polyamic acids advantageously resulting in compositions of high solids but lowered viscosity. Typical end-capping materials are aromatic anhydrides such as phthalic anhydride, naphthalic anhydride and the like. While these agents are effective end-cappers they do little to effect the physical properties of the final polyimides formed using them. As such, the polymers remain difficult to coat, shape and further process.

It would be advantageous to have an end-capping agent that because of its bulkiness would effect the physical properties of polyimides prepared from it.

Compositions of matter have now been discovered that can be used as end-capping agents for the preparation of more easily processable polyimides. These compositions are substituted benzophenone dicarboxylic acids, acid esters and anhydrides.

The aromatic ketones of the present invention are those unsymmetric compounds having the formula

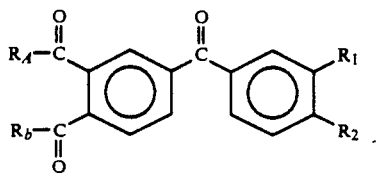

and

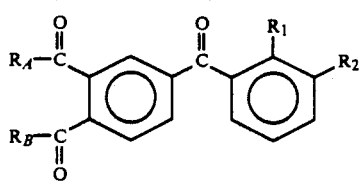

where $R_A$ is the same or different than $R_B$ and are independently the group —OH or $C_1$ to $C_{12}$ linear or branched alkoxy or taken together with the adjacent carbonyl carbons form an anhydride ring, i.e., the compounds

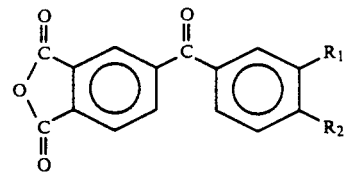

and

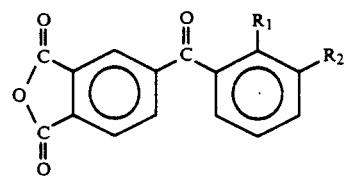

In the above compounds of formula I, the groups $R_1$ and $R_2$ are the same or different and are hydrogen, $C_1$ to $C_6$ linear or branched alkyl, halo, aryl unsubstituted or substituted with one or more aryloxy groups with the proviso that both $R_1$ and $R_2$ cannot be hydrogen. $R_1$ and $R_2$ can also be taken together to form a ring of $(CH_2)_x$ where x is an integer from 3 to 6. Thus rings attached to the aromatic one may be small as cyclopentanyl and up to cyclooctanyl in size.

In the compounds of formula I, it is preferred that $R_A$ and $R_B$ are the same and are the group —OH, $C_1$ to $C_6$ linear or branched alkoxy or the anhydrides illustrated by the compounds of formula IA. Thus, those compounds of formula I can be the free dicarboxylic acids i.e., $R_A=R_B=$—OH or their esters, i.e., $R_A$ and $R_B$ are $C_1$ to $C_6$ alkoxy. Typical esters are the methyl, ethyl, n-propyl, n-butyl, n-pentyl, n-hexyl esters.

In the compounds of the present invention $R_1$ and $R_2$ are the same or different and are the monovalent radicals preferably hydrogen, $C_1$ to $C_3$ linear or branched alkyl, chloro, bromo, phenyl, phenoxyphenyl and, when taken together to form a ring are cyclopentyl or cyclohexyl.

The most preferable of the compounds of the present invention are those of formula IA where $R_1$ and $R_2$ are the same and are methyl, ethyl or chloro.

Illustrative of the compounds of the present invention are the following:

benzophenone-3,4-dimethyl-3',4'-dicarboxylic acid;
benzophenone-3,4-dimethyl-3',4'-dicarboxylic acid dimethyl ester;
benzophenone-3,4-dimethyl-3',4'-dicarboxylic acid diethyl ester;
benzophenone-3,4-diethyl-3',4'-dicarboxylic acid;
benzophenone-3,4-diethyl-3',4'-dicarboxylic acid dimethyl ester;
benzophenone-3,4-diethyl-3',4'-dicarboxylic acid diethyl ester;
benzophenone-3,4-dimethyl-3,'4,'-dicarboxylic acid anhydride;
benzophenone-3,4-diethyl-3',4'-dicarboxylic acid anhydride;
benzophenone-2,3-dimethyl-3',4'-dicarboxylic acid;
benzophenone-2,3-dimethyl-3',4'-dicarboxylic acid dimethyl ester;
benzophenone-2,3-dimethyl-3',4'-dicarboxylic acid diethyl ester;
benzophenone-2,3-diethyl-3',4'-dicarboxylic acid;
benzophenone-2,3-diethyl-3',4'-dicarboxylic acid dimethyl ester;

benzophenone-2,3-diethyl-3',4'-dicarboxylic acid diethyl ester;

benzophenone-2,3-dimethyl-3,'4'-dicarboxylic acid anhydride;

benzophenone-2,3-diethyl-3',4'-dicarboxylic acid anhydride;

benzophenone-3,4-dichloro-3',4'-dicarboxylic acid;

benzophenone-3,4-dichloro-3',4'-dicarboxylic acid; dimethyl ester;

benzophenone-3,4-dichloro-3',4'-dicarboxylic acid; diethyl ester;

benzophenone-3,4-dichloro-3,'4,'-dicarboxylic acid anhydride;

benzophenone-2,3-dichloro-3',4'-dicarboxylic acid;

benzophenone-2,3-dichloro-3',4'-dicarboxylic acid dimethyl ester;

benzophenone-2,3-dichloro-3',4'-dicarboxylic acid diethyl ester; benzophenone-2,3-dichloro-3',4'-dicarboxylic acid anhydride;

As noted earlier the compounds of the present invention are readily prepared by the well known Friedel Crafts acylation procedure, i.e.,

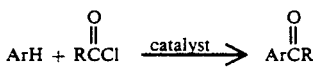

where Ar is an aromatic nucleus and R can be aryl or alkyl.

In such reaction, catalysts are typically of the Lewis or Bronsted acid type. However, in the preferred embodiment of the present invention triflic acid (trifluoromethanesulfonic acid, $CF_3SO_3H$) or similar sulfonic acids have proven to be especially active acylation catalysts. Thus acids known in the art as Super acids such including fluorosulfonic acid, Magic Acid (hydrofluoric acid and antimony pentafluoride) as well as other halo fluoromethanesulfonic acids are useful in causing the reaction to prepare the compounds of the present invention. The following reaction path is illustrative of the method of preparation of the compounds

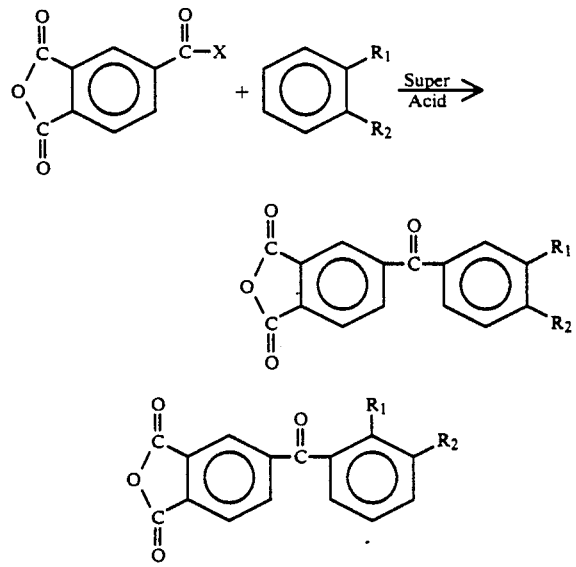

Because these superacids are exceptionally active in causing the acylation to occur as shown above, the general requirement of having a 1:1 mole ratio of acyl halide to Lewis Acid does not apply. Thus, surprisingly small amounts of super acid are effective in causing the acylation reaction. From about 0.1% by weight to about 50% by weight of super acid to acyl halide will catalyze this reaction. Depending on the reactivity of the aromatic hydrocarbon (i.e.) methyl substituted are more reactive than unsubstituted ones; smaller amounts of triflic acid can be used (<0.1% preferred).

As discussed earlier, concerning the amount of $CF_3SO_3H$ necessary to affect the conversion, activated aromatics require lower temperatures than do the deactivated ones. Thus the reaction of o-xylene gives good conversion at about 1.50° C., while o-dichlorobenzene requires considerably higher temperatures (180°-200° C.).

As indicated from the reaction path shown above, the initial reaction to form the compounds of the present invention is a modification of the Friedel Crafts acylation reaction utilizing an anhydride-substituted aromatic acid halide. The product of the reaction is anhydride-substituted benzophenone compounds of formula IA. These compounds can be readily transformed into the compounds of formula I where $R_A$ and $R_B$ are the same or different and are $C_1$ to $C_{12}$ linear or branched alkyl by an alcoholysis reaction, i.e., reaction of the anhydride with an aliphatic alcohol. While the reaction is typically catalyzed by acids e.g., $H_2SO_4$, Lewis Acids or bases, the preferred catalyst is pyridine or a dilute alcoholic solution of an alkali metal hydroxide.

Similarly, rather than alcoholysis, the compounds of formula IA can be converted to the dicarboxylic acids (where $R_A$ and $R_B$ are both the group —OH) by simple hydrolysis e.g., reaction with water. Such reaction may be conducted with or without a catalyst e.g., an organic or inorganic base.

The alcoholysis reaction and the hydrolysis reaction of the anhydride of the compounds of formula IA are well known in the prior art. See for example, the text by March, Advanced Organic Chemistry, McGraw-Hill, New York, N.Y.

Oxidation of compounds of Formula IA where $R_1$ and $R_2$ are alkyl groups can be expected to lead to benzophenone-tetracarboxylic acids, useful monomers that are useful in polyimide preparations.

In order for those skilled in the art to be better able to practice the present invention, the following are given by way of illustration and are not to be taken as limiting the scope of the invention in any way.

EXAMPLE

1. Preparation of benzophenone-3,4-dimethyl-3',4'-dicarboxylic acid:

Stirred a mixture of trimellitic anhydride chloride (10.5 g), o-xylene (22.5 g) and triflic acid (130 mg) at 150° C. bath temperature under a $N_2$ paid for 3 hours, after which the reaction mixture was cooled to room temperature and 25 ml o-xylene and 50 ml of water was added. Under constant stirring a 50% aqueous NaOH solution was slowly added to the reaction mixture until pH was around 12-13. After stopping the agitation the phases were allowed to separate and the organic phase was discarded. The basic aqueous phase was slowly neutralized with con. $H_2SO_4$ until pH 2 and the solid formed was filtered, washed with water and dried in vacuum oven at about 80° C., to give 9.52 g of yellow solid, the GC analysis of which showed two major products in 86:14 ratio. A 1 g sample of this product was digested in a hot dilute IPA solution (50 ml $H_2O$/5 ml IPA) until all the solids dissolved. The solution was then cooled to room temperature and the solid formed was filtered, washed with water and dried at 60°–80° C. for 4 hours in a vacuum oven. 460 mg of shinny pale yellow solid (97% by GC area % analysis) was obtained, whose structure was determined by a combination of GC/MS (exact mass determination of bis-trimethylsilyl derivative of the solid) and $^1H$ and $^{13}C$ NMR spectra. The exact mass is determined as 442.1627 corresponding to $C_{23}H_{30}Si_2O_5$. $^1H$ NMR ($d_6$-DMSO):2.274 (s, 3H, $CH_3$), 2.299 (s, 3H, $CH_3$), 7.30–7.33 (d, 1H, Ar—H), 7.44–747 (doublet of doublet, J=1.4 Hz, J=7.8 Hz, 1H, Ar—H), 7.538 (d, J=1.4 Hz, 1H, Ar—H), 7.763–7.789 (d, J=7.9 Hz, 1H, Ar—H), 7.845–7.877 (doublet of doublet, J=1.7 Hz, J=8.0 Hz, Ar—H), 7.943–7.948 (d, J=1.7 Hz, 1H, Ar—H). The major product of the above reaction was thus determined to be benzophenone-3,4-dimethyl-3',4'-dicarboxylic acid and the total isolated amount of it is 8.2 g (55% yield based on trimellitic anhydride chloride used initially).

2. Preparation of benzophenone-3,4-dichloro-3',4'-dicarboxylic acid:

Stirred a mixture of trimellitic anhydride chloride (10.72 g), o-dichlorobenzene (14.46 g) and triflic acid (1.04 g) at 180° C. bath temperature under a $N_2$ pad for 3 hours. GC analysis of this mixture showed about 50% conversion of the starting material. The bath temperature of the reaction mixture was increased to 200° C. and stirring continued at that temperature for another 3 hours after which the reaction mixture was analyzed by GC to show about 88% conversion. Continued heating for another 3 hours at 200° C. did not change the conversion much. The reaction mixture was cooled to room temperature and 25 ml of toluene and 50 ml of water were added to the reaction. Slowly the product mixture was neutralized with aqueous sodium hydroxide until pH 11–12 and allowed to settle. The top organic phase was discarded and the bottom aqueous phase was neutralized with con. $H_2SO_4$ to pH 2. The precipitated solid was filtered washed with water and dried in vacuum oven at 80° C. overnight to give 9.53 g which upon GC analysis showed two products in the ratio of 86:14. 5 g of the solid was added to 50 ml water and 1.6 g NaOH pellet was added and the mixture stirred until the solution became clear. To this 22 g of a 50% aqueous NaOH solution was dripped in until precipitation occurred. The aqueous slurry was filtered and the residue dissolved in 100 ml water and acidified with con. $H_2SO_4$ to pH 2. The precipitated product was again filtered and dried in vacuum oven at 80° C. for 4 hours to give 3 56 g of darkish solid which upon GC analysis showed a single product. This product was recrystallized from 150 ml boiling water to give 3 g of shinny white solid, (M.P. turns glassy at about 300° C.) the structure of which was determined by a combination of GC/MS (exact mass determination of the bis-trimethylsilyl derivative) and $^1H$ and $^{13}C$ NMR spectra. The exact mass of the compound is 482.0489 corresponding to $C_{21}H_{24}Si_2O_5Cl_2$ for the predominant $^{35}Cl$ isotope. $^1H$ NMR ($d_6$-DMSO): 7.659–7.693 (doublet of doublet, J=1.9 Hz, J=8.3 Hz, 1 H, Ar—H), 7.807–7.835 (d, J=8.3 Hz, 1H, Ar—H), 7.863–7.896 (doublet of doublets, J=1.9 Hz, J=8.0 H, 1H, Ar—H), 7.924–7.931 (d, J=1.9 Hz, 1H, Ar—H), 8.119–8.146 (d, J=8.0 Hz, 1H, Ar—H), 8.323–8.328 (d, J=1.9 Hz, 1H, Ar—H). The structure of the major product was thus determined to be benzophenone-3,4-dichloro-3,'4,'-dicarboxylic acid and the total isolated amount of it is 8.2 g (47% yield based on trimellitic anhydride chloride initially used).

3. Preparation of anhydride from benzophenone-3,4-dichloro-3',4'-dicarboxylic acid:

A 1.02 g sample of benzophenone-3,4-dichloro-3',4'-dicarboxylic acid from above (working example 2) was heated at 200° C. with a slow stream of $N_2$ sweep for 2.5 hours. The sample was cooled to room temperature and weighed again to give 0.94 g of dirty white solid (M.P turns glassy at 300° C.) the structure of which was determined by exact mass determination which was 319.9648 corresponding to $C_{15}H_6O_4Cl_2$ for the predominant $^{35}Cl$ isotope. Meaningful NMR data could not be obtained due to possible hydrolysis of the anhydride moiety in DMSO-d6, resulting in a NMR spectrum containing both the anhydride and the corresponding free acid. Experimental error that may have been introduced into above analysis is because of equipment interaction indicates that the actual yield of anhydride may be somewhat lower than reported above.

What is claimed:

1. Compounds of the formula

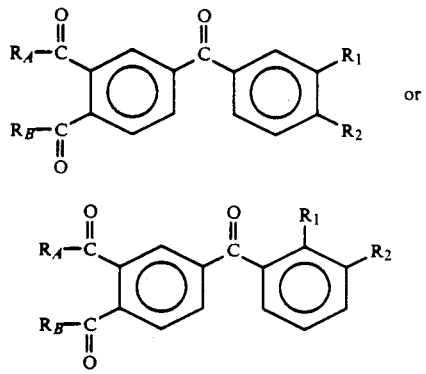

where $R_A$ and $R_B$ are taken together with the adjacent carbonyl carbons form an anhydride ring, $R_1$ and $R_2$ are the same or different and are, $C_1$ to $C_6$ linear or branched alkyl, halo, phenyl unsubstituted or optionally substituted by phenoxy, or $R_1$ and $R_2$ taken together are $(CH_2)_x$ where x is an integer from 3 to 6.

2. The compounds in accordance with claim 1 wherein $R_A$ and $R_B$ taken together with the adjacent carbonyl groups form an anhydride ring.

3. The compounds in accordance with claim 2 wherein $R_1$ and $R_2$ are the same and are $C_1$ to $C_6$ linear or branched alkyl.

4. The compounds in accordance with claim 3 wherein $R_1$ and $R_2$ are the same and are methyl, ethyl or n-propyl.

5. The compounds in accordance with claim 4 wherein $R_1$ and $R_2$ are methyl.

6. The compounds in accordance with claim 2 wherein $R_1$ and $R_2$ are the same and are halo.

7. The compounds in accordance with claim 6 wherein $R_1$ and $R_2$ are the same and are chloro.

* * * * *